(12) United States Patent
Myhrene et al.

(10) Patent No.: US 12,426,549 B2
(45) Date of Patent: Sep. 30, 2025

(54) PLANT TREATMENT ASSEMBLY AND ASSOCIATED METHOD

(71) Applicant: Moleda AS, Sylling (NO)

(72) Inventors: Ole Myhrene, Sylling (NO); Marten Barel, Eindhoven (NL)

(73) Assignee: Moleda AS, Sylling (NO)

( * ) Notice: Subject to any disclaimer, the term of this patent is extended or adjusted under 35 U.S.C. 154(b) by 613 days.

(21) Appl. No.: 17/908,211

(22) PCT Filed: Mar. 15, 2021

(86) PCT No.: PCT/EP2021/056535
§ 371 (c)(1),
(2) Date: Aug. 30, 2022

(87) PCT Pub. No.: WO2021/185763
PCT Pub. Date: Sep. 23, 2021

(65) Prior Publication Data
US 2023/0078025 A1 Mar. 16, 2023

(30) Foreign Application Priority Data
Mar. 16, 2020 (NO) .............................. NO20200314

(51) Int. Cl.
*A01G 7/06* (2006.01)
*A61L 2/07* (2006.01)

(52) U.S. Cl.
CPC . *A01G 7/06* (2013.01); *A61L 2/07* (2013.01)

(58) Field of Classification Search
CPC ........... A01G 7/06; A61L 2/0023; A61L 2/07; A01M 1/2094
See application file for complete search history.

(56) References Cited

U.S. PATENT DOCUMENTS

| 2005/0108920 A1 | 5/2005 | Takenoshita et al. |
| 2016/0174475 A1 | 6/2016 | Mirzakhani Nafchi |

FOREIGN PATENT DOCUMENTS

| EP | 0221580 A1 | 5/1987 |
| JP | 2009225715 A | 10/2009 |

(Continued)

OTHER PUBLICATIONS

Brown, et al., "The Effects of Heat Treatment on the Gene Expression of Several Heat Shock Protein Genes in Two Cultivars of Strawberry"; International Journal of Fruit Science, 2016, vol. 16, No. S1, 239-248.

(Continued)

*Primary Examiner* — Timothy C Cleveland
(74) *Attorney, Agent, or Firm* — Bradley Arant Boult Cummings LLP

(57) ABSTRACT

Plant heat treatment assembly (100) for elimination of pathogens on living plants, comprising a process chamber (1) with inlet (3) and outlet (5), a pre-chamber (4) with pre-chamber inlet (7) and outlet (6). The pre-chamber outlet communicates with the process chamber inlet. A pump (9) is arranged between the process chamber outlet (5) and the pre-chamber inlet (7), circulating gas through the process chamber. A gas heating arrangement (19) has water steam supply. A choking arrangement (11) is between the pre-chamber and the process chamber. The plant heat treatment assembly (100) has a temperature sensor (45) and an adjustable steam supply valve (21) to govern the supply of water steam based on input from the temperature sensor (45). The choking arrangement (11) is adjustable. A method is also disclosed.

12 Claims, 3 Drawing Sheets

(56) References Cited

FOREIGN PATENT DOCUMENTS

| WO | WO-9507612 A1 | 3/1995 |
| WO | WO-2013012311 A1 | 1/2013 |
| WO | WO-2019239888 A1 | 12/2019 |

OTHER PUBLICATIONS http://www.myhrene.no/plantsauna.html, [online] last accessed Aug. 26, 2022.

Stensvand, Arne, 7ForebyggelseafmeldugangrebmedUVbehandling ogrobotteriNorgemmvedArneStensvand.pdf, presentation dated Nov. 7, 2019, 35 pages, downloaded from the web Jun. 29, 2020.

Stensvand, Arne, Plantesauna_A_Stensvand_04_03_2020.pdf, presentation dated Mar. 4, 2020, 31 pages, downloaded from the web Jun. 29, 2020.

https://www.nibio.no/tema/plantehelse/integrert-plantevern/metoder/fysiske-bekjempelsesmetoder, dated Jul. 24, 2017, 5 pages, [online], last accessed Aug. 26, 2022.

Forjaz, Alexandra; International Search Report; PCT/EP2021/056535; Dated: May 25, 2021; 4 pages.

PLANT TREATMENT ASSEMBLY AND ASSOCIATED METHOD

TECHNICAL FIELD

The present invention relates to non-chemical treatment of living plants for elimination of plant pathogens and insects. In particular it concerns a method and an assembly for such treatment.

BACKGROUND ART

It is known that living plants can be exposed to elevated heat that will eliminate pathogens while the plants remain alive. For example, it is known to submerge living plants in warm water with a temperature that the plants can tolerate but the plant pathogens and insects cannot.

In the article "*The Effects of Heat Treatment on the Gene Expression of Several Heat Shock Protein Genes in Two Cultivars of Strawberry*", Brown et al., (International journal of fruit science, 2016, Vol. 16, NO. S1, 239-248), a pre-treatment of living strawberry plants is discussed. In this method, the plants are pre-heated at a pre-heating temperature. The pre-heating temperature is an elevated temperature but is somewhat lower than the plant pathogen and insect eliminating temperature. As a result of the pre-heating, the strawberry plants develop a certain protein that enables the plants to withstand the plant pathogen and insect lethal temperature of the main treatment. To heat the strawberry plants, they are lowered into a water bath.

Patent publication EP0221580 discloses an assembly configured for sterilizing materials, such as mineral wool. In this solution, hot steam (170° C.) is circulated through the mineral wool. After two minutes, the mineral wool has reached a temperature of 100° C., thus sterilizing the wool. Furthermore, the publication discloses a solution to ensure that the steam is circulated through the mineral wool, and not bypassing it along possible channels with low flow-resistance. To obtain this result, the process chamber is surrounded by a flexible inner wall that will contact the mineral wool due to reduced pressure in the process chamber.

Publication US2005108920A1 discloses a method for killing insects in harvested fruits by supplying vapor to fruit containers. The temperature of various fruit containers is measured and the containers having low temperature is provided with additional water vapor for increased temperature raise.

Furthermore, publication WO9507612A1 presents a disinfestation treatment chamber for treating commodities like harvested fruit, flowers and vegetables. Vapor is added to the commodities to kill flies and larvae.

Publication WO2013012311A1 discusses sterilization of oil palm fruit by adding steam above atmospheric pressure, using temperatures such as 100° C.

THE INVENTION

According to the present invention, there is provided a method for elimination of plant pathogens and/or insects on living plants, comprising the following steps:
a) arranging a plurality of plants inside a process chamber that comprises a process chamber inlet and a process chamber outlet;
b) reducing the gas pressure inside the process chamber to a treatment pressure by operating a pump connected to the process chamber outlet;
c) elevating the gas temperature inside the process chamber to a target temperature by providing a controlled flow of water steam to the process chamber inlet;
d) after step c), removing the plants from the process chamber
e) recirculating gas from the process chamber through the process chamber outlet, through the pump, into a pre-chamber, and into the process chamber, wherein a choking arrangement is arranged between the pre-chamber and the process chamber. The process chamber inlet is arranged at an inlet portion and the process chamber outlet is arranged at an oppositely arranged outlet portion of the process chamber. The process chamber comprises flexible side walls that extend at least partly between the inlet portion and the outlet portion. Step b) further includes moving the flexible side walls against the plurality of plants as a result of the pressure difference over the flexible walls. The choking arrangement is an adjustable choking arrangement, and the method comprises controlling the flow of gas and/or the pressure in the process chamber by controlling the choking arrangement.

By using a gas that is supplied with water steam to heat the plants, one obtains a uniform distribution of the heat transfer from the gas to the plants.

Furthermore, the use of pressure difference and the circulation of gas also contributes in an even distribution of heat transfer.

Step c) can in some embodiments comprise providing said flow of water steam to the recirculation flow between the pump and the choking arrangement.

By performing this step, one ensures that the gas circulating through the process chamber flows in engagement with the plants that shall be heated, instead of along a bypass path without significant engagement with the plants. This ensures uniform heating of the plants and thus that all plants are heat treated.

According to the first aspect of the invention, the target temperature inside the process chamber can preferably be below 60° C.

In some embodiments, step c) can comprise controlling the temperature in the process chamber by controlling steam supply to the gas flowing into the process chamber.

This manner of temperature control for heat-treatment of living plants enables the operator to control the plant temperature with accuracy and effectiveness.

In such embodiments, step c) may include controlling steam supply to the gas flowing into the process chamber by operating a steam supply valve based on input from a temperature sensor. Advantageously, the temperature sensor can be arranged in the pre-chamber.

Preferably, step c) comprises supplying water steam to the gas such that the relative humidity of the gas in the process chamber is 100%.

Furthermore, in some embodiments the method can include pressurizing the gas that is circulated with the pump.

In some embodiments of the method according to the invention, the plants are strawberry plants. In such embodiments, the method can include a pre-heating phase, wherein the strawberry plants are heated to about 37° C. before a subsequent period with a cooler temperature, typically 20-25° C. After the subsequent period of cooler temperature, the strawberry plants can be heated to a target temperature of about 40 to 44° C. The pre-heating phase will harden the strawberry plants, enabling them to tolerate the target temperature of about 40 to 44° C. The target temperature can typically be held for a period of about 1 to 4 hours, or 2 to 4 hours.

The method according to the invention can be performed for instance for elimination of one or more of the following pathogens: powdery mildew, angular leaf spot, anthracnose, grey mould, crown rot, and strawberry mites.

According to a second aspect of the present invention, there is provided a plant heat treatment assembly configured for elimination of plant pathogens and/or insects on living plants by treating the plants with heated gas. The plant heat treatment assembly comprises a process chamber that comprises a process chamber inlet and a process chamber outlet, a pre-chamber that comprises a pre-chamber inlet and a pre-chamber outlet, wherein the pre-chamber outlet is in communication with the process chamber inlet. The assembly further comprises a pump arranged between the process chamber outlet and the pre-chamber inlet, the pump being configured to circulate gas through the process chamber. The assembly also comprises a gas heating arrangement comprising a water steam supply and a choking arrangement arranged between the pre-chamber and the process chamber. The process chamber inlet is arranged at an inlet portion and the process chamber outlet is arranged at an oppositely arranged outlet portion of the process chamber. The process chamber comprises flexible side walls that extend at least partly between the inlet portion and the outlet portion and that constitute a separation between the pre-chamber and the process chamber. According to the second aspect of the invention, the plant heat treatment assembly further comprises a temperature sensor and an adjustable steam supply valve configured to govern the supply of water steam based on input from the temperature sensor. The choking arrangement is adjustable.

With such an assembly, the operator is enabled to heat-treat stacks of plants in an efficient and uniform fashion, while having an accurate control of the temperature.

In some embodiments, the assembly according to the second aspect of the invention may comprise a control unit configured to control the steam supply valve based on the input from the temperature sensor, wherein the control unit is set to provide a target temperature that is below 60° C.

Advantageously, the temperature sensor can be arranged in the pre-chamber.

Advantageously, the temperature sensor can be arranged upstream with respect to the process chamber inlet, such as at the pre-chamber outlet or at another position in the pre-chamber. Moreover, there may be more than one sensor.

Furthermore, the choking arrangement can be adjustable by means of a choking actuator. In such embodiments, the choking arrangement can be operated with the control unit.

The chocking arrangement can comprise a base rail having a plurality of base apertures and an adjustment rail comprising a plurality of adjustment apertures. The degree of overlap between the base apertures and the adjustment apertures can be adjustable by sliding the adjustment rail with respect to the base rail.

Advantageously, there may be a choking actuator configured to slide the adjustment rail with respect to the base rail.

In some embodiments, the assembly can further comprise an air intake with an air intake valve, and a circulation line with a circulation line valve, wherein the circulation line valve is arranged between the process chamber outlet and the air intake.

It shall be noted that while the term pump is used herein, the term includes different embodiments of a pump. Thus, the pump can for instance be in the form of a fan.

Tests have shown that with the assembly according to the second aspect of the invention, the operator is able to reach a target temperature in a stack of plants with a tolerance of about 0.5° C. (i.e. a real temperature within +/−0.5° C. from the target temperature).

The assembly will be applicable to heat treatment of strawberry plants. However, heat treatment of other types of plants will also be possible, for instance onions.

DETAILED DESCRIPTION OF THE INVENTION

While the invention has been discussed in general terms above, a more detailed and non-limiting example of embodiment will be presented in the following with reference to the drawings, in which FIG. 1 is a schematic diagram of a plant treatment assembly according to the invention;

Figure 1:
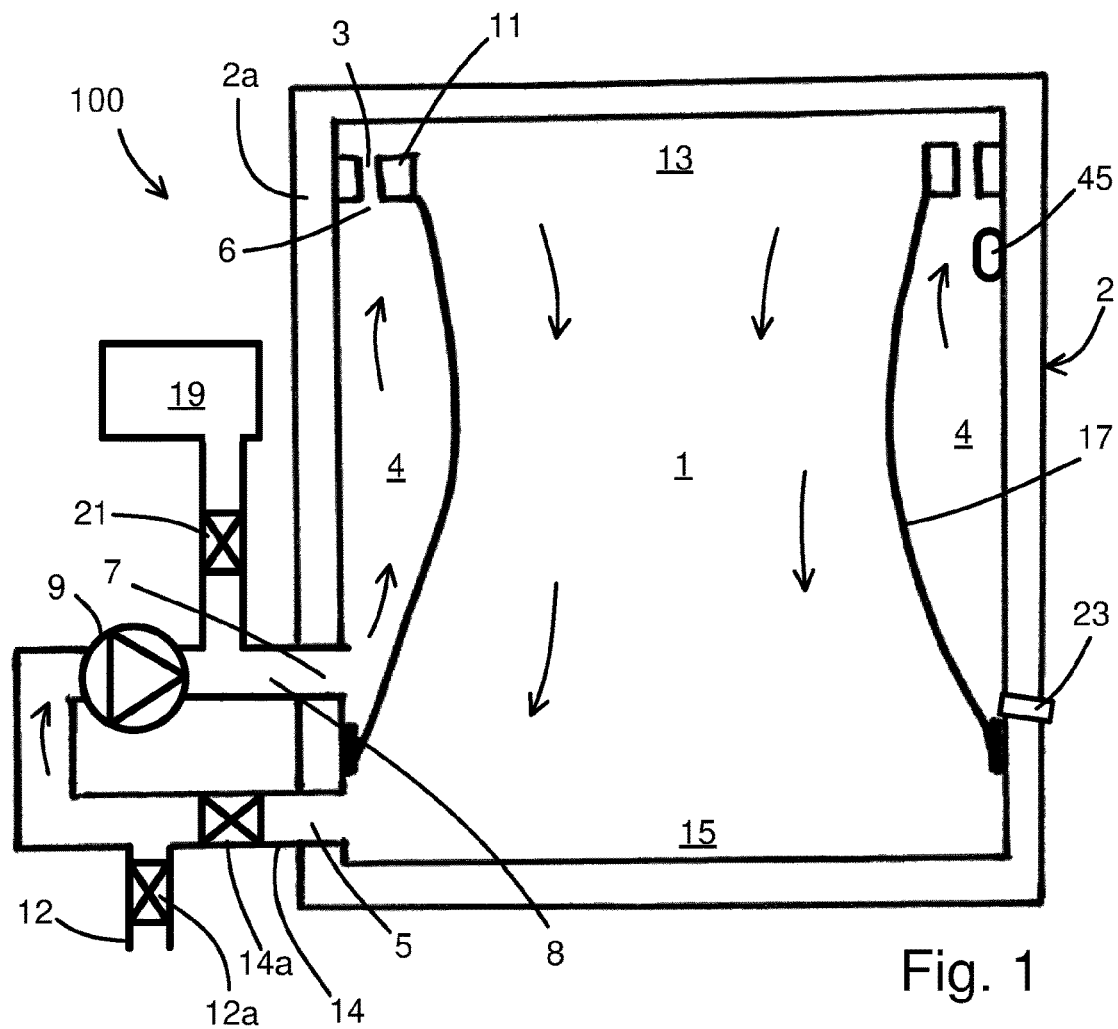

FIG. 1 shows a schematic illustration of a plant heat treatment assembly 100 according to the invention. The assembly 100 has a process chamber 1 configured to receive a plurality of living plants (not shown). Typically, the plants can be stacked on a pallet that can be moved into and out from the process chamber 1 with a forklift. Alternatively, or in addition, there may be arranged rollers 25 (FIG. 2) on the floor of the process chamber 1, to facilitate movement of the plants. The process chamber 1 has a process chamber inlet 3 and a process chamber outlet 5.

In this embodiment, the process chamber 1 is arranged inside a main enclosure 2, which in the shown embodiment is box-shaped with rigid walls, roof and bottom. In some embodiments the main enclosure 2 may be in the form of a container.

Also inside the main enclosure 2 is a pre-chamber 4. The pre-chamber 4 has a pre-chamber outlet 6 that communicates with the process chamber inlet 3. Furthermore, the pre-chamber 4 has a pre-chamber inlet 7.

A pump 9 or fan is connected to the process chamber outlet 5. When the pump 9 is operated, it pumps gas out from the process chamber 1, through the process chamber outlet 5.

In the shown embodiment, the outlet of the pump 9 is connected to the pre-chamber inlet 7. An inlet line 8 connects the pump 9 to the pre-chamber inlet 7. As now will be appreciated by the skilled person, when the pump 9 is operated, gas is circulated through the pump 9, the process chamber 1 and the pre-chamber 4.

Between the pre-chamber 4 and the process chamber 1, there is arranged a choking arrangement 11. The choking arrangement 11 is configured to let gas flow from the pre-chamber 4 into the process chamber. The choking arrangement 11 is configured to provide a pressure drop. Consequently, when the pump 9 is operated, there will be a larger pressure in the pre-chamber 4 than in the process chamber 1.

Connected to the inlet line 8 is a heating arrangement 19. The heating arrangement 19 comprises a steam supply that is configured to provide hot water steam to the gas flow in the inlet line 8. To control the supply of steam, an adjustable steam supply valve 21 can be arranged.

Still referring to FIG. 1, the process chamber inlet 3 is arranged at an inlet portion 13, while the process chamber outlet 5 is arranged at an outlet portion 15. The inlet portion 13 and the outlet portion 15 are oppositely arranged with respect to the process chamber 1. In the shown embodiment, the inlet portion 13 is at a vertically upper portion, while the outlet portion 15 is arranged at a vertically lower portion. Thus, circulated gas will flow through the process chamber 1 in a substantially vertical direction.

Extending between the inlet portion 13 and the outlet portion 15 are flexible side walls 17. Since the gas pressure in the pre-chamber 4 is larger than in the process chamber 1, the flexible side walls 17 will flex inwardly. When a plurality of plants, typically a pallet with a stack of plants, is arranged in the process chamber 1, the flexible walls 17 will move into engagement with the stack of plants. This ensures that the gas flowing from the inlet portion 13 towards the outlet portion 15 will flow through the stack of plants instead of flowing past the plants, such as between the stack and the rigid side walls of the main enclosure 2. In this manner, the operator can control the temperature of the plants and ensure that all the plants are simultaneously heated with the warm gas.

As will be discussed in better detail further below, condensed water may accumulate in the pre-chamber 4. Thus, a drain valve 23 is arranged at a lower portion of the pre-chamber 4.

A temperature sensor 45 is arranged in the pre-chamber 4. Advantageously, the temperature sensor 45 can be arranged close to the pre-chamber outlet 6, as shown in FIG. 1.

Figure 2:
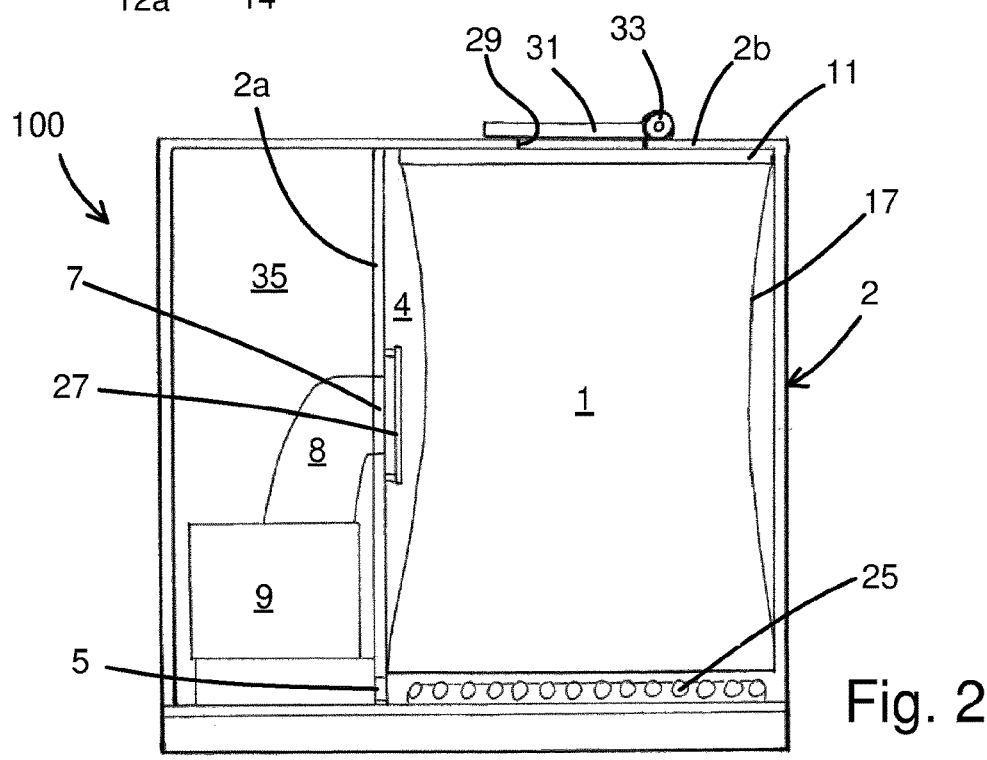
FIG. 2 is a cross section side view of a more realistic embodiment of the assembly.

FIG. 2 is another, more realistic, side view of a plant heat treatment assembly 100 according to the invention. In this view, the rollers 25 configured for movement of pallets (not shown) are shown.

Also shown in FIG. 2 is a pre-chamber inlet plate 27. When the pump 9 is in operation, the gas (i.e. typically air with added steam) will be directed onto the pre-chamber inlet plate 27 and thus be distributed in the pre-chamber 4. The pre-chamber inlet plate 27 ensures that the added steam is evenly distributed in the air or gas supplied to the process chamber 1.

The pre-chamber inlet plate 27 is attached to the inner face of an inlet side wall 2a of the main enclosure 2, in which the pre-chamber inlet 7 is located. As shown in FIG. 2, there is some distance between the pre-chamber inlet plate 27 and the said inlet side wall 2a. The inflowing gas thus flows through a slit or gap between the inlet side wall 2a and the pre-chamber inlet plate 27.

In a top roof 2b of the main enclosure 2 there is provided a top aperture 29. The top aperture 29 is sealingly covered with a top hatch 31. The top hatch 31 can be closed and opened with a hatch actuator 33. When the top hatch 31 is in the open position, ambient air can flow freely into the process chamber 1.

The main enclosure 2 has a utility chamber 35, inside which the pump 9 is located. The heating arrangement 19 can also be arranged in the utility chamber 35.

Figure 3:
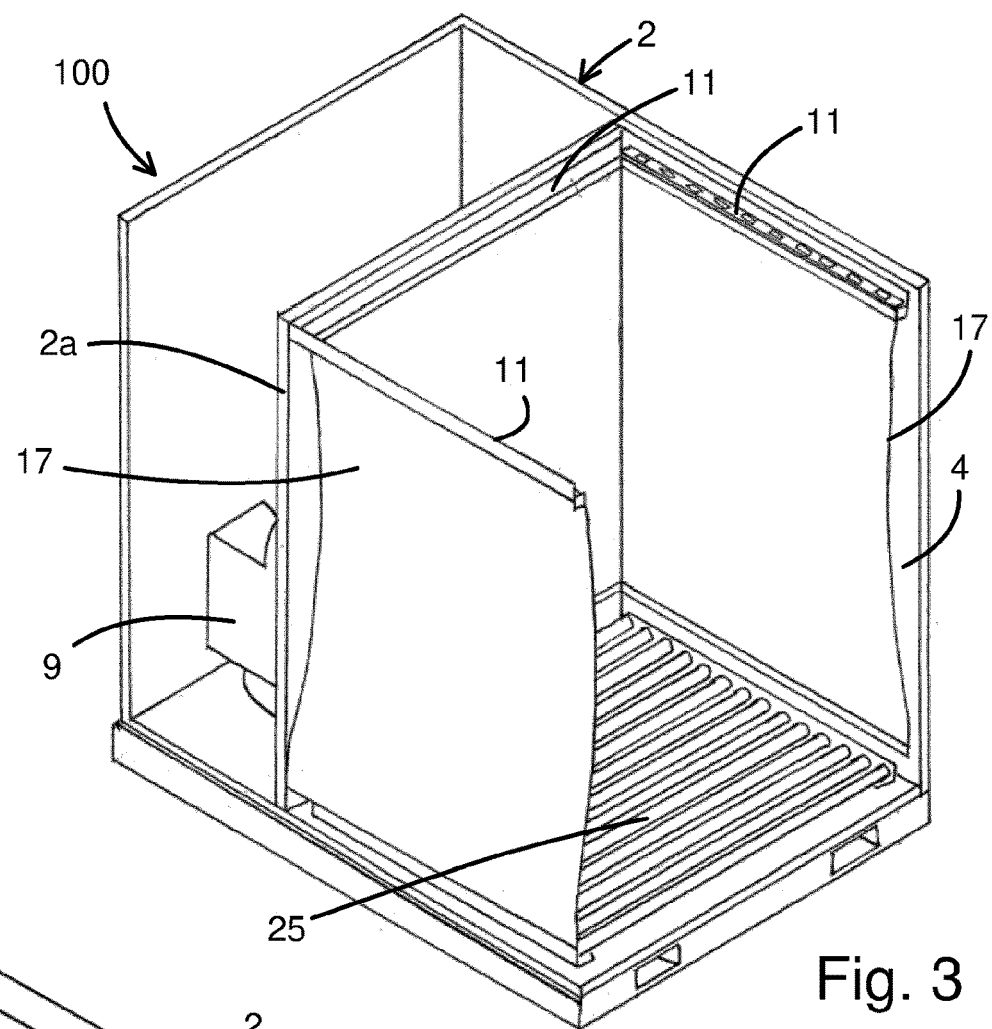
FIG. 3 is a perspective view of the assembly shown in FIG. 2, with some parts removed for illustrational purpose.

FIG. 3 shows the plant heat treatment assembly 100 with a perspective view and with some parts removed for illustrational purpose.

Figure 4:
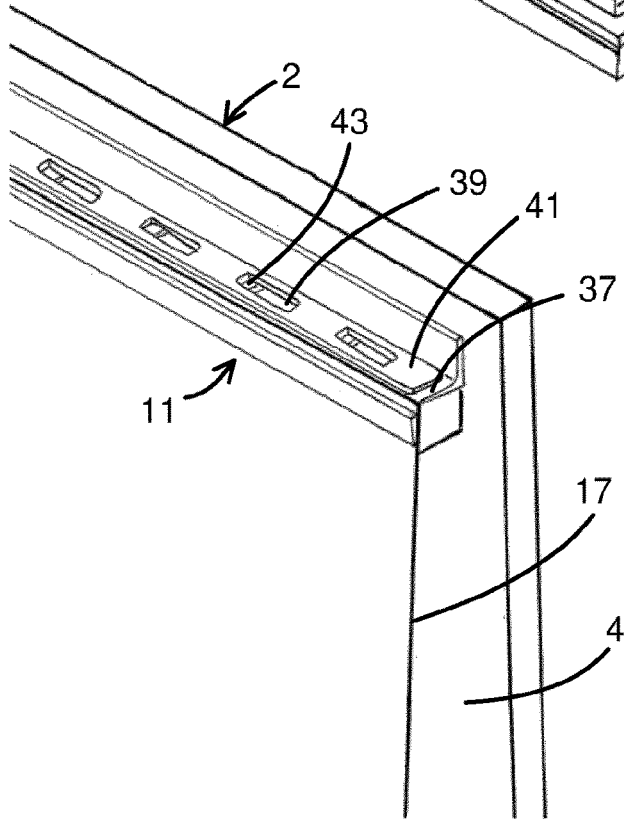
FIG. 4 is an enlarged portion of FIG. 3.

FIG. 4 is an enlarged perspective view for illustration of the function of the choking arrangement 11. The choking arrangement 11 comprises a base rail 37 which is fixed with respect to the main enclosure 2. The base rail 37 comprises a plurality of base apertures 39, which are distributed along the length of the base rail 37. An adjustment rail 41 is arranged in parallel with and in engagement with the base rail 37. The adjustment rail 41 comprises a plurality of adjustment apertures 43.

The adjustment rail 41 is configured to slide with respect to the base rail 37, so that the degree of overlap between the base apertures 39 and the adjustment apertures 43 changes. Since the overlap between the base apertures 39 and the adjustment apertures 43 governs the flow aperture through the choking arrangement 11, sliding of the adjustment rail 41 changes the degree of choking.

Although not shown in FIG. 4, a choking actuator can be arranged to slide the adjustment rail 41. Such a choking actuator can typically be a hydraulically, pneumatically or electrically operated actuator.

Although not well shown in the drawings, the chocking arrangement 11 can advantageously be distributed along all four of the upper edges of the process compartment 1. This provides an even distribution of gas flowing from the pre-chamber 4 into the process chamber 1.

Figure 6:
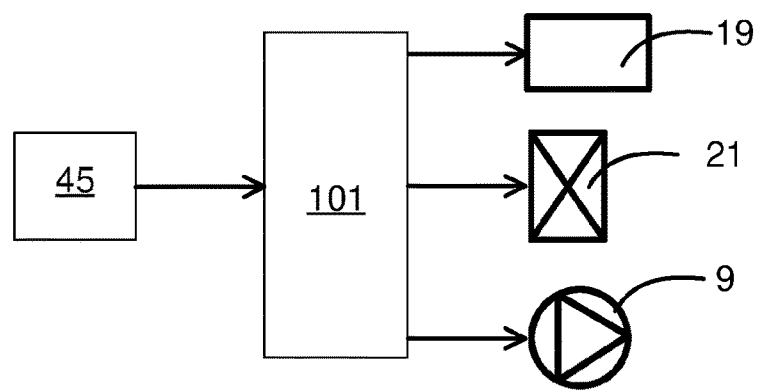
FIG. 6 is a schematic diagram illustrating a control unit and components connected to the control unit.

Advantageously, the operation of the pump 9, the heating arrangement 19, and the choking arrangement 11 can be automatically operated by a control unit 101, schematically shown in FIG. 6. The control unit 101 can typically be a computer or similar electric control device which can be programmed to run a pre-defined heating process. Moreover, the control unit 101 can advantageously be fed with input from one or more temperature sensors 45. The steam supply valve 21 can then be operated by the control unit 101, on the basis of input from the temperature sensor 45. In some embodiments, the control unit 101 can advantageously also control one or more of the pump 9, the heating arrangement 19, the hatch actuator 33, and/or the choking arrangement 11.

Since the plant heat treatment assembly 100 according to the invention is configured for heat treatment of living plants, temperature control is crucial. The relation between temperature, relative humidity, and pressure in the process chamber can be used to control the temperature of the plants.

In some embodiments, the plants may have a temperature of about 0° C. or even frozen (e.g. −1° C.) when entering the process chamber 1. When adding the treatment gas, typically air with added water steam, water will effectively condense on the cold plants and thus transfer energy to the plants, which are thus effectively heated. Using gas with added water steam ensures that water immediately condenses on the plants in the process chamber, due to the pressure drop over the choking arrangement 11. This provides a good distribution of the energy transfer to the plants, compared to a passive flow of gas through a process chamber that has a substantially atmospheric pressure.

In some embodiments, the treatment gas (i.e. typically air with added water steam) inserted into the pre-chamber 4 can hold the target temperature, for instance 37° C.

Tests wherein the heating arrangement 19 comprises a water steam supply has revealed that the temperature inside the process chamber 1 may rise even after the supply of steam has been stopped. Furthermore, the tests have shown that by operating the choking arrangement 11, this effect can be eliminated. In other words, by suitable control of the adjustable choking arrangement 11 after the steam supply has been cut off, one can prevent excessive heating of the living plants inside the process chamber 1.

By raising the pressure in the process chamber 1 (such as by reducing "under-pressure"), the gas present in the process chamber can hold more water steam and thus the condensation on the plants is reduced. This limits further heating of the plants. Such a pressure rise can be obtained by opening the choking arrangement 11 or by reducing or halting the speed of the pump 9.

During the process, the surface of the living plants will be wet. The dew point in the process chamber 1 is lower than in the pre-chamber 4 because of the reduced pressure. When the desired temperature inside the process chamber 1 has been reached, the plants are wet but there is normally no free water present.

Advantageously, the temperature of the circulating gas can be monitored in the pre-chamber, such as at the position of the pre-chamber outlet 6. A temperature sensor 45 for this purpose is schematically depicted in FIG. 1. Even when a target temperature reached in the pre-chamber 4, for instance 37° C., condensation will appear immediately when the gas enters the process chamber 1, due to the lower pressure.

Condensed water may appear on the flexible walls 17, on the faces that face the pre-chamber 4. This water may accumulate in the pre-chamber 4 and can be drained with the drain valve 23.

Some embodiments may involve pressurization of the circulating path of the gas. By pressurizing the gas, one can obtain a higher pressure in the pre chamber while still having a pressure drop over the choking arrangement 11. For instance, one can have an absolute pressure of 1.2 bar (atmosphere) inside the process chamber 1 while having an absolute pressure of 1.4 bar (atmosphere) inside the pre-chamber 4. By using a high pressure, e.g. a pressure above 1 the ambient pressure (being typically about 1 atmosphere), the operator is enabled to let more steam into the gas and thus increase the energy transfer rate to the plants.

This can for instance be performed by pressurizing the pre-chamber 4 and the process chamber 1 by pulling in ambient air before starting the circulation. As shown in FIG. 1, there is an air intake 12 in communication with the inlet side of the pump 9. The air intake 12 is provided with an air intake valve 12a. Furthermore, extending between the process chamber outlet 5 and the inlet side of the pump 9, there is a circulation line 14. The circulation line 14 is provided with a circulation line valve 14a.

By closing the circulation line valve 14 and opening the air intake valve 12a, the pump 9 can be used to increase the gas pressure in the pre-chamber 4 and process chamber 1. When the pressure has been increased, the air intake valve 12a is closed and the circulation line valve 14a is opened. Gas will then be circulated at an elevated pressure.

Advantageously, the air intake valve 12a and the circulation line valve 14a can be controlled by the control unit 101.

Figure 5:
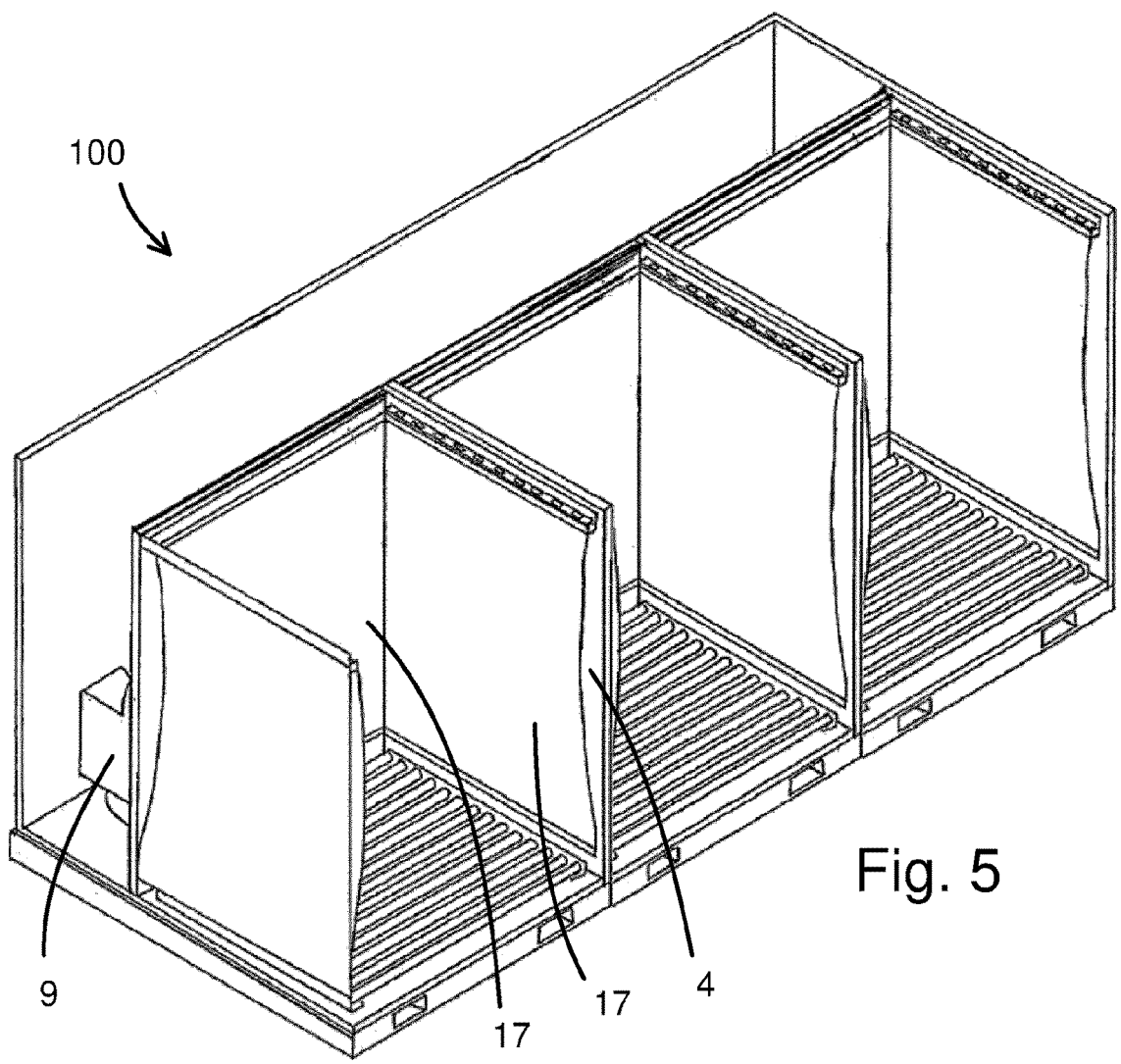
FIG. 5 is a perspective view illustrating an embodiment where the assembly according to the invention comprises a plurality of process chambers.

FIG. 5 depicts an embodiment of the invention wherein the plant heat treatment assembly 100 comprises a plurality of process chambers. Advantageously, in some embodiments there may be arranged one pump 9 and one heating arrangement 19 that is configured to operate on all the process chambers 1. In this way, several stacks of plants can be treated simultaneously. In other embodiments, however, each process chamber 1 and pre-chamber 4 can be operated with a dedicated pump 9 and heating arrangement 19. That will increase cost but will enable dedicated adjustment of the process in the specific process chambers.

The plant heat treatment process discussed herein and the assembly for performing such a process will be applicable typically for target temperatures (heated temperatures) of 30 to 50° C., or even 30 to 60° C.

Typical maximum temperatures or target temperatures, to which the living plants are heated, can be below 39, 37, or 35 degrees C. The maximum temperature will depend on the type of plant that is heat treated, and on the specific process that is used.

LIST OF REFERENCE NUMBERS 1 process chamber
2 main enclosure
2a inlet side wall
2b top roof
3 process chamber inlet
4 pre-chamber
5 process chamber outlet
6 pre-chamber outlet
7 pre-chamber inlet
8 inlet line
9 pump
11 choking arrangement
12 air intake
12a air intake valve
13 inlet portion
14 circulation line
14a circulation line valve
15 outlet portion
17 flexible walls
19 heating arrangement
21 steam supply valve
23 drain valve
25 rollers
27 pre-chamber inlet plate
29 top aperture
31 top hatch
33 hatch actuator
35 utility chamber
37 base rail
39 base aperture
41 adjustment rail
43 adjustment aperture
45 temperature sensor
100 plant heat treatment assembly
101 control unit

The invention claimed is:

1. A method for elimination of plant pathogens and/or insects on living plants, the method comprising:
   a) arranging a plurality of plants inside a process chamber that comprises a process chamber inlet and a process chamber outlet;
   b) reducing the gas pressure inside the process chamber to a treatment pressure by operating a pump connected to the process chamber outlet;
   c) elevating the gas temperature inside the process chamber to a target temperature by providing a controlled flow of water steam to the process chamber inlet;
   d) after step c), removing the plants from the process chamber;
   e) recirculating gas from the process chamber through the process chamber outlet, through the pump, into a pre-chamber, and into the process chamber, wherein a choking arrangement is arranged between the pre-chamber and the process chamber,
   wherein the process chamber inlet is arranged at an inlet portion and the process chamber outlet is arranged at an oppositely arranged outlet portion of the process chamber,
   wherein the process chamber comprises flexible side walls extending at least partly between the inlet portion and the outlet portion, and wherein step b) further includes moving the flexible side walls against the plurality of plants as a result of the pressure difference over the flexible walls, and wherein the choking arrangement is an adjustable choking arrangement, and wherein the method comprises controlling the flow of gas and/or the pressure in the process chamber by controlling the choking arrangement.

2. The method according to claim 1, wherein step c) comprises providing said flow of water steam to the recirculation flow between the pump and the choking arrangement.

3. The method according to claim 1, wherein the target temperature inside the process chamber is below 60° C.

4. The method according to claim 1, wherein step c) comprises controlling the temperature in the process chamber by controlling steam supply to the gas flowing into the process chamber.

5. The method according to claim 4, wherein controlling steam supply to the gas flowing into the process chamber is performed by operating a steam supply valve on the basis of input from a temperature sensor.

6. The method according to claim 1, wherein step c) comprises supplying water steam to the gas such that the relative humidity of the gas in the process chamber is 100%.

7. The method according to claim 1, wherein the method comprises pressurizing the gas that is circulated with the pump.

8. A plant heat treatment assembly configured for elimination of plant pathogens and/or insects on living plants by treating the plants with heated gas, the plant heat treatment assembly comprising:
   a process chamber that comprises a process chamber inlet and a process chamber outlet;
   a pre-chamber that comprises a pre-chamber inlet and a pre-chamber outlet, wherein the pre-chamber outlet is in communication with the process chamber inlet;
   a pump arranged between the process chamber outlet and the pre-chamber inlet, configured to circulate gas through the process chamber;
   a gas heating arrangement comprising a water steam supply;
   a choking arrangement arranged between the pre-chamber and the process chamber;
   wherein the process chamber inlet is arranged at an inlet portion and the process chamber outlet is arranged at an oppositely arranged outlet portion of the process chamber,
   wherein the process chamber comprises flexible side walls that extend at least partly between the inlet portion and the outlet portion and that constitute a separation between the pre-chamber and the process chamber;
   wherein the plant heat treatment assembly further comprises
   a temperature sensor;
   an adjustable steam supply valve configured to govern the supply of water steam based on input from the temperature sensor wherein the choking arrangement is adjustable.

9. The plant heat treatment assembly according to claim 8, comprising a control unit configured to control the steam supply valve based on the input from the temperature sensor, wherein the control unit is set to provide a target temperature below 60° C.

10. The plant heat treatment assembly according to claim 8, wherein the temperature sensor is arranged in the pre-chamber.

11. The plant heat treatment assembly according to claim 8, wherein the chocking arrangement comprises a base rail having a plurality of base apertures and an adjustment rail comprising a plurality of adjustment apertures, wherein the degree of overlap between the base apertures and the adjustment apertures is adjustable by sliding the adjustment rail with respect to the base rail.

12. The plant heat treatment assembly according to claim 8, wherein comprising an air intake with an air intake valve, and a circulation line with a circulation line valve, wherein the circulation line valve is arranged between the process chamber outlet and the air intake.

* * * * *